United States Patent [19]

Scarlett et al.

[11] Patent Number: 5,387,753
[45] Date of Patent: Feb. 7, 1995

[54] PROCESS FOR THE PREPARATION OF ALCOHOLS AND DIOLS

[75] Inventors: John Scarlett, Spennymoor; Michael W. M. Tuck, London; Michael A. Wood, Middlesbrough, all of England

[73] Assignee: Eastman Chemical Company, Kingsport, Tenn.

[21] Appl. No.: 174,319

[22] Filed: Dec. 30, 1993

[30] Foreign Application Priority Data

Dec. 2, 1993 [GB] United Kingdom ............... 9324823

[51] Int. Cl.$^6$ .................. C07C 27/04; C07C 31/135; C07C 31/18; C07C 33/14
[52] U.S. Cl. .................................. 568/864; 568/814; 568/822; 568/830; 568/831; 568/840; 568/861
[58] Field of Search ............ 568/822, 823, 831, 861, 568/864, 830, 840

[56] References Cited

U.S. PATENT DOCUMENTS

| | | | |
|---|---|---|---|
| 2,040,944 | 5/1936 | Lazier | 568/814 |
| 2,079,414 | 5/1937 | Lazier | 568/864 |
| 2,091,800 | 8/1937 | Adkins et al. | 568/864 |
| 2,105,664 | 1/1938 | Lazier | 568/864 |
| 2,137,407 | 11/1938 | Lazier | 568/831 |
| 2,755,317 | 7/1956 | Kassel . | |
| 2,818,393 | 12/1957 | Lefrancois et al. . | |
| 2,830,095 | 4/1958 | Nicolaisen | 570/206 |
| 2,884,450 | 4/1959 | Holmquist | 568/831 |
| 2,901,466 | 8/1959 | Kibler et al. | 568/864 |
| 2,917,549 | 12/1959 | Hasek et al. | 568/831 |
| 3,334,149 | 8/1967 | Akin et al. | 568/831 |
| 4,032,458 | 6/1977 | Cooley et al. | 568/864 |
| 4,052,467 | 10/1977 | Mills et al. | 568/881 |
| 4,172,961 | 10/1979 | Henery et al. | 568/864 |
| 4,268,695 | 5/1981 | Lange et al. | 568/864 |
| 4,361,710 | 11/1982 | Weitz et al. | 568/864 |
| 4,584,419 | 4/1986 | Sharif et al. | 568/864 |
| 4,652,685 | 5/1987 | Cawse et al. | 568/831 |
| 4,751,334 | 6/1988 | Turner et al. | 568/864 |
| 4,837,368 | 6/1989 | Gustafson et al. | 568/881 |
| 4,918,248 | 4/1990 | Hattori et al. | 568/885 |
| 4,929,777 | 5/1990 | Irick, Jr. et al. | 568/864 |
| 4,999,090 | 3/1991 | Tateno et al. | 568/822 |
| 5,030,771 | 7/1991 | Fuhrmann et al. | 568/831 |
| 5,124,435 | 6/1992 | Mori et al. | 528/307 |
| 5,142,067 | 8/1992 | Wegman et al. | 549/326 |
| 5,185,476 | 2/1993 | Gustafson | 568/831 |
| 5,191,091 | 3/1993 | Wegman et al. | 549/326 |

FOREIGN PATENT DOCUMENTS 143634  6/1985  European Pat. Off. .
241760 10/1987  European Pat. Off. .

(List continued on next page.)

OTHER PUBLICATIONS

Mansour et al., "Sel. Hydrog. of Esters to Alcoh. with a Catal. Obtained Rh$_2$O$_3$, Sn (n–C$_4$H$_9$)$_4$ and SiO$_2$ and Based On Isol. Active Centres", *Angew. Chem.* 101, (1989) Nr. 3, 360–63.

(List continued on next page.)

Primary Examiner—Werren B. Lone
Attorney, Agent, or Firm—J. Frederick Thomsen; Harry J. Gwinnell

[57] ABSTRACT

A process is described for reactivating an at least partially deactivated copper-containing ester hydrogenation catalyst which has undergone deactivation through use in hydrogenation of an unsaturated organic compound selected from esters of C$_8$ to C$_{22}$ monocarboxylic acids, diesters of dicarboxylic acids, and lactones, to yield a corresponding hydroxylic compound selected from alcohols and diols which comprises contacting the at least partially deactivated copper-containing catalyst at an effective reactivation temperature and for an effective period of time with a stream of hydrogen-containing gas which is substantially free from the unsaturated organic compound thereby to reactivate the at least partially deactivated copper-containing catalyst.

16 Claims, 1 Drawing Sheet

FOREIGN PATENT DOCUMENTS

| | | | |
|---|---|---|---|
| 0285786 | 10/1988 | European Pat. Off. | 568/831 |
| 301853 | 2/1989 | European Pat. Off. | |
| 353990 | 2/1990 | European Pat. Off. | |
| 378756 | 7/1990 | European Pat. Off. | |
| 552463 | 7/1993 | European Pat. Off. | |
| 1276722 | 10/1961 | France | |
| 1144703 | 3/1963 | Germany | |
| 1159925 | 12/1963 | Germany | |
| 2719867 | 11/1978 | Germany | |
| 3843956 | 6/1990 | Germany | |
| 4141199 | 6/1993 | Germany | |
| 879264 | 10/1961 | United Kingdom | 568/831 |
| 988316 | 4/1965 | United Kingdom | |
| 1024318 | 3/1966 | United Kingdom | |
| 1454440 | 11/1976 | United Kingdom | |
| 1464263 | 2/1977 | United Kingdom | |
| 2116552 | 9/1985 | United Kingdom | |
| 2250287 | 6/1992 | United Kingdom | |
| 03854 | 11/1982 | WIPO | |
| 03189 | 6/1986 | WIPO | |
| 07358 | 12/1986 | WIPO | |
| 00937 | 2/1988 | WIPO | |
| 00886 | 2/1989 | WIPO | |
| 08121 | 7/1990 | WIPO | |
| 01961 | 2/1991 | WIPO | |

OTHER PUBLICATIONS

Wehner & Gustafson, "Catalytic Hydrog. of Esters Over Pd/ZnO", *Journ. of Catalysis*, 135, 420–426 (1992).

Lewin et al., "Fiber Chemistry", pp. 8–9 (1985).

Martyn V. Twigg, "Catalyst Handbook", 2nd Ed., p. 54.

Homer Adkins, "Catal. Hydrog. of Esters to Alcoh.", *Organic Reactions*, vol. 8, Chp. 1, pp. 2–27 (1954).

Freifelder, "Catal. Hydrog. in Org. Synth.", pp. 129–151.

Kirk–Othmer, *Encl. of Chem. Tech.*, 3rd Ed., vol. 1, pp. 733–739.

PROCESS FOR THE PREPARATION OF ALCOHOLS AND DIOLS

FIELD OF THE INVENTION

This invention relates to a process for the production of a hydroxylic compound selected from alcohols and diols by hydrogenation of a corresponding unsaturated organic compound selected from esters, diesters and lactones.

BACKGROUND OF THE INVENTION

Various processes have been described for the production of alcohols and diols by hydrogenation of a corresponding unsaturated organic compound selected from esters, diesters and lactones in the presence of a heterogeneous ester hydrogenation catalyst. Such unsaturated organic compounds are unsaturated by virtue of their possessing a carbon-to-oxygen double bond in the linkage —(CO)—O—. They do not need to possess any further unsaturated linkages. Hydrogenation processes of this type are thus applicable to a wide variety of esters, diesters and lactones which contain no unsaturation apart from the afore-mentioned carbon-to-oxygen double bond, for example monoesters of $C_8$ to $C_{22}$ alkylcarboxylic acids, diesters of $C_4$ to $C_{16}$ dicarboxylic acids, and lactones of hydroxycarboxylic acids containing 4 to 16 carbon atoms. However, the presence of further unsaturation in the molecule is not excluded. Thus there can also be used in such processes esters, diesters and lactones which contain further unsaturation in the molecule, for example monoesters of unsaturated $C_8$ to $C_{22}$ aliphatic carboxylic acids, diesters of unsaturated aliphatic or alicyclic carboxylic acids, and unsaturated lactones.

Examples of such hydrogenation processes, many of which are conventionally conducted in the liquid phase, include hydrogenation of alkyl esters of aliphatic monocarboxylic acids to alkanols, and of dialkyl esters of aliphatic dicarboxylic acids to aliphatic diols. It has also been proposed in some cases to effect the hydrogenation reaction under vapour phase reaction conditions.

It is known to produce the cycloaliphatic diol cyclohexanedimethanol by hydrogenation of the corresponding cycloaliphatic diester, usually a dialkyl cyclohexanedicarboxylate, which may itself be produced by hydrogenation of the corresponding dialkyl benzenedicarboxylate, for example dimethyl terephthalate.

A commercial hydrogenation catalyst used for hydrogenation of carboxylic acid esters is copper chromite which may optionally be promoted with barium and/or manganese. The use of such a catalyst in a process for the production of butane-1,4-diol is disclosed in EP-A-0143634. In WO-A-82/03854 there is disclosed a process for effecting the hydrogenolysis of carboxylic acid esters which involves the use of a catalyst comprising a reduced mixture of copper oxide and zinc oxide. Other catalysts useful in hydrogenation reactions which may be mentioned are the palladium/zinc-containing catalysts of WO-A-89/00886 and the mixed catalyst systems of EP-A-0241760. Manganese promoted copper catalysts have also been offered for sale as hydrogenation catalysts.

The hydrogenation reactor or reactors may be operated adiabatically or isothermally with external or internal cooling. Adiabatic reactors are used where possible for preference since they are usually cheaper to construct and to operate than an isothermal reactor of shell and tube design.

The hydrogenation of an ester, diester or lactone feedstock is generally an exothermic reaction. In a liquid phase reaction the feedstock is normally diluted with an inert diluent, conveniently with recycled product hydroxylic compound, and the catalyst is wholly wetted with liquid. The diluent acts as a heat sink and helps to prevent the danger of damage to the catalyst due to the exothermic nature of the hydrogenation reaction.

In a typical vapour phase hydrogenation process the unsaturated organic compound, i.e. the ester, diester or lactone, is normally vaporised directly into a hot hydrogen-containing gas to give a vaporous mixture, which may be heated further or diluted with more hot hydrogen-containing gas in order to raise its temperature above the dew point. It is normally essential to ensure that the vaporous mixture in contact with the catalyst is above its dew point, i.e. above that temperature at which a mixture of gases and vapour just deposits liquid as a fog or a film. This dew point liquid will normally contain all the condensable components of the vapour phase, as well as dissolved gases, in concentrations that satisfy the usual vapour/liquid criteria. It may include the starting material, an intermediate product, a by-product and/or the final hydrogenation product. Generally the process is operated so that the temperature of the vaporous feed mixture is above its dew point, for example about 5° C. to about 10° C. above its dew point. Moreover it is desirable to prevent contact of droplets of liquid with the catalyst, particularly droplets which are rich in the unsaturated organic compound, because damage to the catalyst may result from loss of mechanical strength, from formation of hot spots on the surface of the catalyst or in the pores of the catalyst, due to the exothermic nature of the reaction, leading possibly to sintering and thereby to loss of chemically effective catalyst surface area (particularly in the case of copper-containing catalysts), or from disintegration of the catalyst pellets possibly as a result of explosive vaporisation within the pores of the pellets. Hydrogenation reactor conditions which aim to prevent premature degradation of the hydrogenation catalyst by mechanisms such as the formation of hot spots on the catalyst surface are described in WO-A-91/01961.

Notwithstanding the precautions which may be taken, as described for example in WO-A-91/01961, to maximise the active life of a hydrogenation catalyst, it is still recognised in the art that a hydrogenation catalyst is generally subjected to conditions in the hydrogenation zone which lead inexorably to significant deactivation, and possibly also to irreversible loss of catalytic activity, over a period of time. Such deactivation may be ascribed to different causes in different hydrogenation reactions. For example deposition of carbon or carbonaceous materials on the catalyst surface may be a cause of loss of catalyst activity. In addition to such deactivation processes the catalyst pellets may disintegrate physically in the course of time leading to formation of fines which tend to block the pathway for vapour through the catalyst bed and to lead to an unacceptable increase in pressure drop across the catalyst bed. The deactivation processes may be slowed but not readily reversed.

In any commercial hydrogenation process, the catalyst will eventually lose activity and/or selectivity and need to be replaced with a fresh charge of catalyst.

There may be many unrelated but complementary causes of catalyst deactivation in a hydrogenation reaction. These may include i) deposition of carbonaceous materials on the catalyst surface, ii) comminution or structural deterioration of the catalyst pellets resulting from localised physical conditions, iii) poisoning of the catalyst, particularly by compounds containing chlorine or sulphur atoms, and iv) sintering of the catalyst, particularly when the catalyst is a copper-containing catalyst, at high temperatures, for example at temperatures greater than about 230° C.

It is generally recognised in the art that, in hydrogenation reactions utilising copper-containing catalysts, the catalyst is readily deactivated due, it is thought, to sintering or due to migration of metal and is also prone to physical loss of strength such that the catalyst granules tend to disintegrate into a fine powder. Thus it is regarded that catalyst deactivation of copper-containing hydrogenation catalysts is irreversible. Thus, for example, attempts to reactivate copper-containing catalysts which have undergone deactivation as result of prolonged use in the liquid phase hydrogenation of dimethyl 1,4-cyclohexanedicarboxylate according to the teachings of U.S. Pat No. 3,334,149 have not been successful.

Any hydrogenation process which permits reversal or deceleration of deactivation processes is likely to have significant commercial advantages over the processes taught in the prior art due to lower catalyst consumption costs. Such a process would further provide significant environmental benefits resulting from a reduction in catalyst turnover.

SUMMARY OF THE INVENTION

It is therefore an object of the present invention to provide a process for reactivation of an ester hydrogenation catalyst after it has suffered a loss of catalytic activity during a period of use in the hydrogenation of an ester, diester, or lactone. It is further an object of the present invention to provide a process for hydrogenating an unsaturated organic compound selected from esters of $C_8$ to $C_{22}$ monocarboxylic acids, diesters of dicarboxylic acids, and lactones, to produce a corresponding alcohol or diol, wherein the life of the copper-containing catalyst used therein may be prolonged by its periodic reactivation.

According to the present invention there is provided a process for reactivating an at least partially deactivated copper-containing ester hydrogenation catalyst which has undergone deactivation through use in hydrogenation of an unsaturated organic compound selected from esters of $C_8$ to $C_{22}$ monocarboxylic acids, diesters of dicarboxylic acids, and lactones, to yield a corresponding hydroxylic compound selected from alcohols and diols which comprises contacting the at least partially deactivated copper-containing catalyst at an effective reactivation temperature and for an effective period of time with a stream of hydrogen-containing gas which is substantially free from the unsaturated organic compound thereby to reactivate the at least partially deactivated copper-containing catalyst.

The process of the invention is used to especially good effect for reactivating partially deactivated copper-containing ester hydrogenation catalysts which have been utilised in hydrogenation processes utilising vapour phase feed conditions. Thus the invention further provides a process for the production of a hydroxylic compound selected from alcohols and diols by hydrogenation of a corresponding unsaturated organic compound selected from esters, diesters and lactones which comprises:

(a) providing a hydrogenation zone containing a charge of a granular copper-containing ester hydrogenation catalyst;

(b) supplying to the hydrogenation zone, in a first phase of operation, a vaporous feed stream comprising a hydrogen-containing gas and an unsaturated organic compound selected from esters, diesters and lactones;

(c) maintaining the hydrogenation zone, in the first phase of operation, under temperature and pressure conditions conducive to hydrogenation of the unsaturated organic compound to yield the hydroxylic compound;

(d) recovering from the hydrogenation zone, in the first phase of operation, a reaction product stream comprising the hydroxylic compound;

(e) supplying to the hydrogenation zone, in a second phase of operation, a stream of hydrogen-containing gas which is substantially free from the unsaturated organic compound at an effective reactivation temperature and for an effective period of time thereby to reactivate the charge of copper-containing ester hydrogenation catalyst therein.

The process of the invention can be used for reactivating copper-containing ester hydrogenation catalysts which have been used for effecting hydrogenation of essentially any vaporisable ester, diester, or lactone that has an appreciable vapour pressure, e.g. about 0.01 psia (about 0.001 bar) or more, at the feed temperature to the respective hydrogenation zone or zones, and that does not deposit elemental carbon on the catalyst.

Typically the ester, diester or lactone contains up to about 30 carbon atoms.

The unsaturated organic compound is preferably selected from monoesters of $C_8$ to $C_{22}$ alkylcarboxylic acids, diesters of $C_4$ to $C_{16}$ dicarboxylic acids, and lactones of hydroxycarboxylic acids containing 4 to 16 carbon atoms, as well as monoesters of unsaturated $C_8$ to $C_{22}$ aliphatic carboxylic acids, diesters of unsaturated aliphatic or alicyclic carboxylic acids, and unsaturated lactones.

Examples of hydrogenation reactions involving the use as feedstock of an ester, diester or lactone, to which the teachings of the present invention can be applied include the processes taught in WO-A-91/01961, in EP-A-0143634, in WO-A-86/03189, and in WO-A-86/07358.

The unsaturated organic compound may be a di-($C_1$ to $C_4$ alkyl) ester of a dicarboxylic acid containing at least 4 carbon atoms. Thus in one preferred process the unsaturated organic compound is a dialkyl ester of a $C_4$ dicarboxylic acid, for example, a dialkyl maleate, and the corresponding hydrogenation product is butane-1,4-diol, gamma-butyrolactone or tetrahydrofuran or a mixture of two or more thereof. In such a process the copper-containing catalyst is preferably a reduced copper chromite catalyst, a reduced promoted copper chromite catalyst, or a reduced manganese promoted copper catalyst. The dialkyl maleate normally is a di-($C_1$ to $C_4$ alkyl) maleate and is preferably dimethyl maleate or diethyl maleate.

A similar reaction is the hydrogenation of gamma-butyrolactone to yield butane-1,4-diol or the hydrogenation of epsilon-caprolactone to yield hexane-1,6-diol.

The unsaturated organic compound may be a di-($C_1$ to $C_4$ alkyl) cyclohexanedicarboxylate, for example dimethyl cyclohexanedicarboxylate, while the hydrogenation product is cyclohexanedimethanol. Thus in a particularly preferred process the unsaturated organic compound is dimethyl 1,4-cyclohexanedicarboxylate and the hydrogenation product is 1,4-cyclohexanedimethanol. Other reactions to which the process of the invention is applicable include hydrogenation of a di-($C_1$ to $C_4$ alkyl) 1,2- or 1,3-cyclohexanedicarboxylate, for example dimethyl 1,2- or 1,3-cyclohexanedicarboxylate, to 1,2- or 1,3-cyclohexanedimethanol respectively.

As another type of unsaturated organic compound which can be used as starting material in the process of the present invention there can be mentioned esters, for example $C_1$ to $C_4$ alkyl esters, of $C_8$ to $C_{22}$ monocarboxylic acids. Typical esters include the methyl and ethyl esters of $C_8$ to $C_{22}$ alkylcarboxylic acids, such as methyl laurate, methyl oleate, methyl stearate, methyl linoleate and the like.

The granular catalyst used in the process of the invention may be any copper-containing catalyst capable of catalysing hydrogenation or hydrogenolysis of an ester to the corresponding alcohol or mixture of alcohols. It may be formed into any suitable shape, e.g. pellets, rings or saddles.

Typical copper-containing ester hydrogenation catalysts include copper-on-alumina catalysts, reduced copper oxide/zinc oxide catalysts, with or without a promoter, manganese promoted copper catalysts, and reduced copper chromite catalysts, with or without a promoter. Suitable copper oxide/zinc oxide catalyst precursors include CuO/ZnO mixtures wherein the Cu:Zn weight ratio ranges from about 0.4:1 to about 2:1. An example is the catalyst precursor bearing the designation DRD 92/71. Promoted copper oxide/zinc oxide precursors include CuO/ZnO mixtures wherein the Cu:Zn weight ratio ranges from about 0.4:1 to about 2:1 which are promoted with from about 0.1% by weight up to about 15% by weight of barium, manganese or a mixture of barium and manganese. Such promoted CuO/ZnO mixtures include the Mn-promoted CuO/ZnO precursor available under the designation DRD 92/92. Suitable copper chromite catalyst precursors include those wherein the Cu:Cr weight ratio ranges from about 0.1:1 to about 4:1, preferably from about 0.5:1 to about 4:1. Catalyst precursors of this type are the precursors available under the designation DRD 89/21 or under the designation PG 85/1. Promoted copper chromite precursors include copper chromite precursors wherein the Cu:Cr weight ratio ranges from about 0.1:1 to about 4:1, preferably from about 0.5:1 to about 4:1, which are promoted with from about 0.1% by weight up to about 15% by weight of barium, manganese or a mixture of barium and manganese. Manganese promoted copper catalyst precursors typically have a Cu:Mn weight ratio of from about 2:1 to about 10:1 and can include an alumina support, in which case the Cu:Al weight ratio is typically from about 2:1 to about 4:1. An example is the catalyst precursor DRD 92/89.

All of the above mentioned catalysts available under the general designations DRD or PG can be obtained from Davy Research and Development Limited, P.O. Box 37, Bowesfield Lane, Stockton-on-Tees, Cleveland TS18 3HA, England.

Any recognised supporting medium may be used to provide physical support for the copper-containing catalyst used in the process of the invention. This support can be provided by materials such as zinc oxide, alumina, silica, alumina-silica, silicon carbide, zirconia, titania, carbon, a zeolite, or any suitable combination thereof.

The copper-containing catalysts that are particularly preferred for use in the process of the invention are the reduced forms of the copper chromite, promoted copper chromite, and manganese promoted copper catalyst precursors described hereinabove.

In the reactivation step the at least partially deactivated copper-containing hydrogenation catalyst is treated with a stream of hydrogen-containing gas thereby to reactivate the copper-containing catalyst. Normally it will be preferred to carry out this step at elevated temperatures, typically at a temperature of about 150° C. or more up to about 350° C. In this step the feed temperature to the hydrogenation zone may be lower than, for example about 10° C. to about 50° C. lower than, substantially equal to, or higher than, e.g. about 10° C. to about 50° C. higher than, the feed temperature to the hydrogenation zone of the vaporous feed stream. Preferably the feed temperature to the hydrogenation zone during the reactivation step is within about 30° C. from the feed temperature to the hydrogenation zone of the vaporous feed stream. Thus during the reactivation step the feed temperature may be from about 10° C. to about 30° C. lower than, or from about 10° C. to about 30° C. higher than, the feed temperature to the hydrogenation zone of the vaporous feed stream.

The stream of hydrogen-containing gas used in the reactivation step may comprise a hot stream of recycle gas and conveniently comprises a hot stream of recycle and make-up gas. The feed pressure during this reactivation step can be the same as, lower than, or higher than the feed pressure used in step (b). Conveniently it is substantially the same as the feed pressure used in step (b).

Preferably the vaporous feed stream of step (b) is at a temperature at least about 5° C. above its dew point.

The hydrogenation zone may comprise a shell-and-tube reactor which may be operated under isothermal, or near isothermal, conditions with the copper-containing catalyst in the tubes and the coolant in the shell or vice versa. Usually, however, it will be preferred to use an adiabatic reactor since these are cheaper to construct and install than shell-and-tube reactors. Such an adiabatic reactor may contain a single charge of a copper-containing hydrogenation catalyst or may contain two or more beds of copper-containing catalyst, or beds of different copper-containing hydrogenation catalysts. If desired, external or internal inter-bed heat exchangers may be provided in order to adjust the feed temperature to one or more beds of copper-containing catalyst downstream from the inlet to the adiabatic hydrogenation reactor.

In the process of the invention there can be used two or more hydrogenation zones in parallel, at least one of which is at any time on line and the other or others of which is or are in reactivation mode. When there are only two zones then one zone will be on line while the other is in reactivation mode. If the plant has three or more zones, then one or more of the zones will usually be in reactivation mode, while one or more others is or are on line. Alternatively, if the plant has three or more zones, then at least one zone can be on line, at least one zone can be in standby mode, and at least one zone is in reactivation mode. The number of zones on line and in reactivation or standby mode at any given time will depend on the desires of the plant operator and upon the economic considerations associated with the particular hydrogenation reaction in question.

In a vapour phase hydrogenation process, which is typically strongly exothermic, it is important to ensure that the unsaturated organic compound is above its dew point, and hence in vapour form rather than in liquid form, in the vaporous hydrogen-containing reaction mixture whilst it is in contact with the copper-containing hydrogenation catalyst. In this way the risk of droplets of a liquid phase rich in unsaturated organic compound contacting the copper-containing catalyst and the resulting localised development of "hot spots" and the risk of formation of "fines" due to explosive localised vaporisation of liquid within the pores of the copper-containing catalyst are minimised.

In the vaporous feed stream of step (b) the hydrogen-containing gas:unsaturated organic compound molar ratio can vary within wide limits, depending upon the temperature, pressure, and the volatility of the unsaturated organic compound. Although the major gaseous constituent is hydrogen, other gases may also be introduced, normally in minor amount, in the hydrogen-containing gas supplied as make-up gas to the process, such as nitrogen, argon, methane, and carbon oxides. The less volatile that the unsaturated organic compound is the lower will be its vapour pressure at a given temperature and the higher the hydrogen-containing gas:unsaturated organic compound molar ratio will have to be in order to keep the vaporous feed mixture above its dew point at the relevant temperature. Conversely the more volatile that the unsaturated organic compound is the lower that this molar ratio need be. Usually it will range from about 10:1 up to 8000:1, preferably in the range of from about 200:1 to about 1000:1.

The hydrogen-containing gas used in steps (b) and (e) of the process may comprise fresh make-up gas or a mixture of make-up gas and recycle gas. The make-up gas can be a mixture of hydrogen, optional minor amounts of components such as CO and $CO_2$, and inert gases, such as argon, nitrogen, or methane, containing at least about 70 mole % of hydrogen. Preferably the make-up gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen make-up gas is desired. If gas recycle is utilised in the process then the recycle gas will normally contain minor amounts of one or more products of the hydrogenation reaction which have not been fully condensed in the product recovery stage downstream from the hydrogenation zone. For example, in the hydrogenation of dimethyl cyclohexanedicarboxylate using gas recycle, the gas recycle stream will contain minor amounts of methanol.

Although the process of the invention is operated with the feed stream in the vapour phase, it is convenient to express the feed rate of the unsaturated organic compound to the hydrogenation zone as a space velocity and to express that space velocity as a liquid hourly space velocity. Hence it is convenient to express the feed rate in terms of the ratio of the liquid feed rate of the unsaturated organic compound to the vaporisation zone to the volume of the hydrogenation catalyst. Thus the equivalent liquid hourly space velocity of the unsaturated organic compound through the hydrogenation catalyst is preferably from about 0.05 to about 4.0 $h^{-1}$. In other words it is preferred to feed the liquid unsaturated organic compound to the vaporisation zone at a rate which is equivalent to, per unit volume of catalyst, from about 0.05 to about 4.0 unit volumes of unsaturated organic compound per hour (i.e. about 0.05 to about 4.0 $m^3 h^{-1}$ per $m^3$ of catalyst). Even more preferably the liquid hourly space velocity is from about 0.1 $h^{-1}$ to about 1.0 $h^{-1}$. If the unsaturated organic compound is a solid at ambient temperatures, then it may be necessary to heat it sufficiently to melt it or to dissolve it in a suitable inert solvent, in which latter case the solvent is ignored for the purpose of measuring the liquid hourly space velocity.

It will be readily apparent to those skilled in the art that the rate of passage of the vaporous feed stream through the hydrogenation zone will depend upon the feed rate of the unsaturated organic compound to the vaporisation zone and upon the hydrogen-containing gas:unsaturated organic compound molar ratio.

In step (c) it is preferred to use a feed temperature which is in the range of from about 150° C. to about 350° C., preferably in the range of from about 150° C. to about 300° C. The precise choice of feed temperature will depend on the stability of the unsaturated organic compound undergoing hydrogenation, the activity of the copper-containing catalyst, and the temperature tolerance of the catalyst. In many cases the most preferred feed temperature range is from about 180° C. to about 250° C. However, in the case of hydrogenation of dimethyl 1,4-cyclohexanedicarboxylate the preferred feed temperature is in the range of from about 200° C. to about 260° C.

The feed pressure is preferably in the range of from about 150 psia (about 10.34 bar) up to about 2000 psia (about 137.90 bar). However, the benefits and advantages of the present low pressure process utilising vaporous feed conditions are best realised by carrying out the process at a pressure of from about 450 psia (about 31.03 bar) up to about 1000 psia (about 68.95 bar).

It appears from our work during investigation of the hydrogenation of dimethyl 1,4-cyclohexanedicarboxylate that an explanation for the decline in catalyst activity is that involatile polymeric byproducts are formed on the copper-containing catalyst surface which are themselves susceptible to hydrogenation or hydrogenolysis. Such polymeric byproducts may be, for example, polyesters formed by ester exchange between the feed unsaturated organic compound and a hydroxylic component, e.g. 1,4-cyclohexanedimethanol or an intermediate product such as methyl 4-hydroxymethylcyclohexanecarboxylate. It can be postulated that the high boiling diester thus formed can then undergo further ester exchange reactions leading to involatile polymeric products. Alternatively ethers and polyethers can be formed by reaction between molecules of 1,4-cyclohexanedimethanol to form di-(4-hydroxymethylcyclohexylmethyl) ether which has itself free hydroxyl groups which can form further ether or ester linkages and yield corresponding involatile polyethers or polyester-polyethers.

Analogous polyester, polyether and mixed polyether-polyester products can be envisaged as being formed during hydrogenation of dimethyl maleate, diethyl maleate, diethyl succinate, or dimethyl fumarate to form butane-1,4-diol, during hydrogenation of gamma-butyrolactone to yield butane-1,4-diol, or during hydrogenation of epsilon-caprolactone to form hexane-1,6-diol.

Such polyester, polyether and mixed polyether-polyester by products are capable of being hydrogenated or undergoing hydrogenolysis. It is consistent with our findings to assume that in the reactivation step (e) such involatile polymeric materials themselves undergo hydrogenation or hydrogenolysis to yield more volatile materials such as 1,4-cyclohexanedimethanol, when dimethyl 1,4-cyclo-hexanedicarboxylate has been hydrogenated, or butane-1,4-diol, when a maleate ester or gamma-butyrolactone has been hydrogenated.

In the hydrogenation of an ester of a long chain fatty acid, for example a methyl ester of a $C_8$ to $C_{22}$ aliphatic monocarboxylic acid, the long chain alcohol formed can undergo ester interchange with the starting material to form a $C_8$ to $C_{22}$ alkyl ester of the $C_8$ to $C_{22}$ monocarboxylic acid. It is postulated that this $C_{16}$ to $C_{44}$ ester, which is much less volatile than either the ester starting material or the desired alcohol product, can eventually form a sufficiently thick liquid film on the catalyst surface to cause significant catalyst deactivation through hindering free access of the ester starting material to the active catalytic sites.

The period required for reactivation will depend upon the nature of the hydrogenation reaction, upon the extent of deactivation of the copper-containing catalyst, and upon the volatility of the products of the reactivation procedure, as well as upon the temperature and hydrogen partial pressure prevailing in the hydrogenation zone during the reactivation step. Typically this period may vary from a few minutes, for example about 10 minutes or less, up to a period of days, for example 10 days or more. Normally it will suffice, assuming that favourable temperature and hydrogen partial pressure conditions have been selected, to carry out reactivation for a matter of a few hours, for example from about 1 hour up to about 24 hours.

Figure 1:
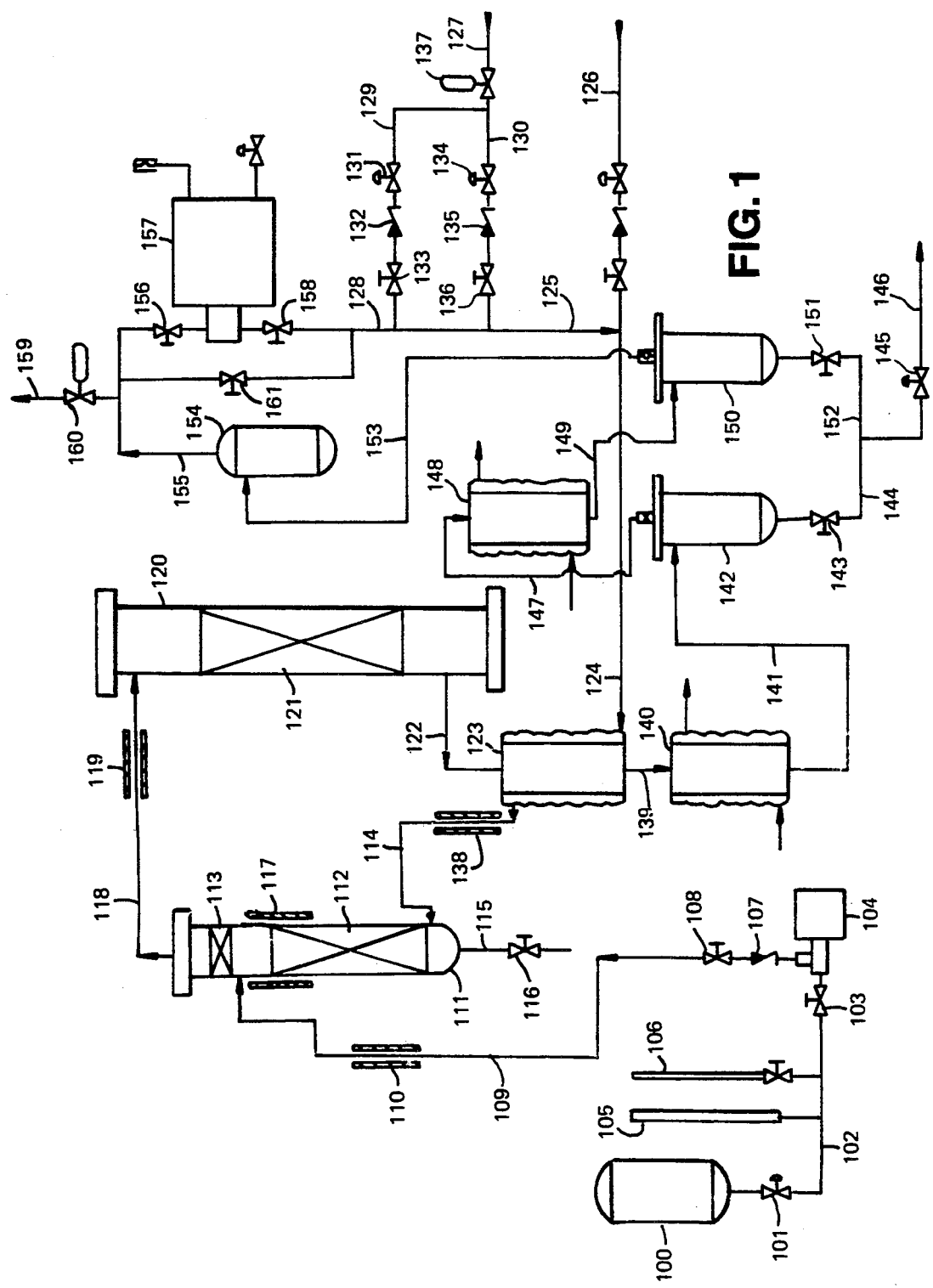
FIG. 1 is a simplified flow diagram of an experimental apparatus for production of 1,4-cyclohexanedimethanol in a single hydrogenation zone by hydrogenation of dimethyl 1,4-cyclohexanedicarboxylate.

It will be understood by those skilled in the art that, whilst dimethyl 1,4-cyclohexanedicarboxylate has been chosen as a suitable material with which to exemplify the process of the invention, the process of the invention is by no means limited in its application to hydrogenation reactions involving dimethyl 1,4-cyclohexanedicarboxylate and may, in fact, be applied to any vapour phase process for hydrogenation of an ester, a diester or lactone in which involatile hydrogenatable byproducts are formed and deposited on the copper-containing catalyst surface, for example hydrogenation of dimethyl or diethyl maleate to yield butane-1,4-diol, of gamma-butyrolactone to yield butane-1,4-diol, or of methyl laurate to yield lauryl alcohol.

The invention is further described with reference to the following Examples. The compositions of copper-containing catalysts A and B used in the Examples are listed in Table I. The oxygen content of the catalyst has been omitted in each case.

TABLE I

| Catalyst | | Composition wt % | | | | | | Surface area m²/g | Density g/cm³ | Pore Volume mm³/g |
|---|---|---|---|---|---|---|---|---|---|---|
| | | Cu | Cr | Zn | Mn | Ba | Al | | | |
| A | DRD89/21 | 57.6 | 19.0 | <0.01 | 0.09 | <0.01 | <0.01 | 28 | 1.420 | 200 |
| B | DRD92/89 | 41.1 | 0.26 | <0.01 | 6.4 | <0.01 | 20.4 | 47.1 | 1.452 | 211 |

Examples 1 to 7

The hydrogenation of a technical grade of dimethyl 1,4-cyclohexanedicarboxylate was investigated using the experimental apparatus illustrated in FIG. 1.

The composition of the technical grade feed was: 34.47 wt % trans-dimethyl 1,4-cyclohexanedicarboxylate, 62.61 wt % cis-dimethyl 1,4-cyclohexanedicarboxylate, 1.50 wt % methyl hydrogen 1,4-cyclohexanedicarboxylate of formula

and 0.05 wt % water, with the balance being impurities including di-4-hydroxymethylcyclohexylmethyl ether of formula

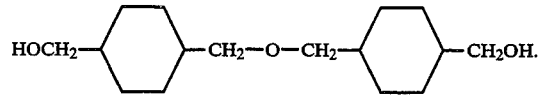

In a commercial plant, hydrogen gas is separated from the hydrogenation product and is advantageously recycled through the hydrogenation zone. The hydrogen recycle stream will contain a quantity of methanol vapour produced by the hydrogenation of dimethyl 1,4-cyclohexanedicarboxylate. Hence, the vaporous mixture supplied to the hydrogenation zone in a commercial plant will generally contain methanol in addition to hydrogen and an unsaturated organic compound. In order that the experimental rig described hereinbelow should accurately predict the results obtained during commercial operation, the liquid feed supplied to the vaporiser was supplemented by a quantity of liquid methanol corresponding to the quantity of methanol which would be contained in the recycle hydrogen stream in a commercial plant. Although hydrogen is recycled in the experimental rig described hereinbelow, the quantity of methanol contained within the recycle hydrogen stream is proportionately less than would be contained in a corresponding commercial recycle stream. This difference arises because the recycle gas in the experimental rig is cooled substantially below the temperature to which it would be desirably cooled in a commercial plant. More methanol is therefore "knocked out" of the experimental recycle hydrogen stream. This discrepancy between the experimental rig and a commercial plant is necessitated by the delicacy of the equipment, particularly the analytical equipment, used in the experimental rig. In these Examples, methanol is added to the experimental liquid feed in a quantity which is substantially equal to the proportionate quantity of methanol which would be present in the experimental recycle stream if the rig were operated under commercial conditions minus the quantity of methanol actually present in the experimental recycle hydrogen stream. In the Examples, all parameters such as conversion rates and hourly space velocities are calculated on a methanol free basis.

The experimental apparatus is illustrated in FIG. 1. An approximately 70 wt % solution of the technical grade of dimethyl 1,4-cyclohexanedicarboxylate in methanol is fed from reservoir 100 by way of valve 101, line 102 and valve 103 to liquid feed pump 104. Burette 105 provides a buffer supply whilst burette 106 is fitted with a liquid level controller (not shown) that controls valve 101 so as to ensure that liquid feed is supplied from reservoir 100 to liquid feed pump 104 at a constant head. The liquid feed is pumped through non-return valve 107 and isolation valve 108 into line 109, which can be heated by electrical heating tape 110, before the heated liquid enters the upper part of an insulated vaporiser vessel 111 above a bed of 6 mm×6 mm glass rings 112. A stainless steel demister pad 113 is fitted at the top end of the vaporiser vessel 111. A stream of hot hydrogen-containing gas is supplied to the bottom of vaporiser 111 in line 114. A liquid drain line 115 fitted with a drain valve 116 enables withdrawal of any unvaporised liquid feed material (e.g. "heavies") from the base of the vaporiser vessel 111. The vaporisation of the liquid feed supplied to the vaporiser vessel 111 is assisted by heating tape 117. A saturated vaporous mixture comprising dimethyl 1,4-cyclohexanedicarboxylate and hydrogen is recovered in line 118 from the top of vaporiser vessel 111. The vaporous mixture is heated by heating tape 119 in order to raise its temperature above the dew point of the mixture prior to entering the top end of hydrogenation reactor 120 which contains a bed of 300 ml (428.1 g) of a pelleted copper chromite hydrogenation catalyst 121. The catalyst was catalyst A of Table I. Glass rings are packed in reactor 120 above and below the catalyst bed 121. The vaporous mixture passes downward through catalyst bed 121 where conversion of dimethyl 1,4-cyclohexanedicarboxylate to 1,4-cyclohexanedimethanol occurs under adiabatic conditions. Adiabaticity is maintained by electrical heating tapes (not shown) embedded within insulation around reactor 120 under the control of appropriately positioned thermocouples (not shown). The overall reaction is mildly exothermic with a general increase in catalyst bed temperature of approximately 1° to 2° C. The hydrogenation product mixture exits the hydrogenation reactor 120 in line 122 and is passed through heat exchanger 123 which simultaneously cools the hydrogenation product mixture and heats a supply of hydrogen-containing gas from line 124. Condensation of the bulk of the 1,4-cyclohexanedimethanol in line 122 occurs in heat exchanger 123. The gas in line 124 comprises hydrogen-containing gas from line 125 and, optionally, an inert gas or a mixture of inert gases such as nitrogen, argon or methane supplied in line 126. The gas in line 125 comprises make-up hydrogen supplied in line 127 and recycle hydrogen supplied in line 128. Make-up hydrogen in line 127 may be supplied to line 125 in either or both of two streams in lines 129 and 130 via a system of pressure controllers 131 to 136 and a mass flow controller 137 from high purity hydrogen cylinders (not shown).

The heated hydrogen-containing gas from heat exchanger 123 passes on in line 114 and is heated further by electrical heating tape 138 for supply to the vaporiser vessel 111.

The cooled hydrogenation product from heat exchanger 123 passes on through line 139 to be cooled further in cooler 140 to a temperature near ambient temperature. The liquid/vapour mixture from cooler 140 passes on in line 141 to a first knockout pot 142 where liquid hydrogenation product is collected for eventual supply by means of valve 143, line 144 and control valve 145 to product line 146. A vaporous mixture comprising hydrogen and uncondensed methanol exits the top of knockout pot 142 in line 147 and is further cooled to a temperature of 10° C. in cooler 148. The further cooled liquid/vapour mixture from cooler 148 is supplied via line 149 to a second knockout pot 150 wherein condensed methanol is collected for eventual supply through valve 151 and line 152 to product line 146. The gas and uncondensed materials from knockout pot 150 are supplied via line 153 through suction pot 154 into line 155 and then through valve 156 to gas recycle compressor 157. Gas is recycled through valve 158 lines 128, 125, 124 and 114 to vaporiser 111. In order to control the concentration of inert gases, such as nitrogen, in the circulating gas a purge gas stream may be bled from the system in line 159 under the control of valve 160.

Reference numeral 161 indicates a bypass valve.

At start up of the apparatus the charge of copper-containing catalyst was placed in reactor 120 which was then purged with nitrogen. The catalyst charge was then reduced according to the teachings of EP-A-0301853.

Technical grade dimethyl 1,4-cyclohexanedicarboxylate, appropriately diluted with methanol, was then pumped to the vaporiser 111 at a feed rate corresponding to an appropriate liquid hourly space velocity. The feed temperature, feed pressure and gas:dimethyl 1,4-cyclohexanedicarboxylate molar ratio in the vaporous mixture in line 118 were selected so that the hydrogenation zone was operated under conditions which prevented the condensation of both dimethyl 1,4-cyclohexanedicarboxylate and the less volatile 1,4-cyclohexanedimethanol product. The temperature in the hydrogenation zone was above the dew point of the vaporous feed mixture at the operating pressure.

The liquid in line 146 was analysed periodically by capillary gas chromatography using a 15 m long, 0.32 mm internal diameter fused silica column coated internally with a 0.25 μm film of DB wax, a helium flow rate of 2 ml/minute with a gas feed split ratio of 100:1 and a flame ionisation detector. The instrument was fitted with a chart recorder having a peak integrator and was calibrated using a commercially available sample of dimethyl 1,4-cyclohexanedicarboxylate of known composition. The exit gas was also sampled and analysed by gas chromatography using the same technique. The identities of the peaks were confirmed by comparison of the retention times observed with those of authentic specimens of the materials in question and by mass spectroscopy. Included amongst the compounds detected in the reaction mixture were 1,4-cyclohexanedimethanol, dimethyl 1,4-cyclohexanedicarboxylate, 4-methoxymethyl cyclohexanemethanol, di-(4-methoxymethylcyclohexylmethyl) ether, and methanol. Operation of the rig was monitored over a period of several weeks. From the results obtained it appeared that over this period dimethyl 1,4-cyclohexanedicarboxylate had been converted in excess of 99%, with a selectivity to 1,4-cyclohexanedimethanol of approximately 98.5% being obtained, the balance being minor by-products. After making due allowance for the methanol present in the feed solution of dimethyl 1,4-cyclohexanedicarboxylate from reservoir 100, 2 moles of methanol were detected for every 1 mole of dimethyl 1,4-cyclohexanedicarboxylate converted in accordance with the stoichiometry of the hydrogenation reaction.

After further operation of the rig the conversion of dimethyl 1,4-cyclohexanedicarboxylate was found to be 97.53% under the conditions specified for Example 1 in Table II below, the selectivity to 1,4-cyclohexanedimethanol being 96.89%. The operating conditions were subsequently altered to those listed under Example 2 in Table II. Operation of the rig was continued for a number of days over the course of which it was necessary to raise the feed temperature by 3° C. in order to maintain the desired conversion of dimethyl 1,4-cyclohexanedicarboxylate. The results observed are listed under Example 3 in Table II. A further period of continuous operation of the rig ensued during which the activity declined over the course of several weeks, as evidenced by the increase in feed temperature of 6° C., compared with Example 2, necessary to maintain the conversion of dimethyl 1,4-cyclohexanedicarboxylate as near as possible the desired value. The results at this time are given under Example 4. Operation was continued for a few days more. Then the conditions were changed to those set out in Table II under Example 5, which are comparable to those specified for Example 1. Compared with Example 1 the conversion had dropped over the intervening period of operation from 97.53% to 85.47%, thus demonstrating that a very significant loss of catalyst activity had occurred. The dimethyl 1,4-cyclohexanedicarboxylate feed was then turned off and, after an interval of approximately 3 hours, the feed temperature to reactor 120 was increased to 250° C. and hydrogen gas was passed through the reactor 120 at this temperature for 14 hours in order to effect catalyst reactivation. The reactor 120 was then returned to the same conditions as those which prevailed immediately prior to the reactivation step. The dimethyl 1,4-cyclohexanedicarboxylate conversion immediately after catalyst reactivation had occurred was 91.86% as reported in Example 6, demonstrating that at least partial reactivation had been successfully accomplished. This was confirmed by restoring the operating conditions substantially to those of Example 4. The conversion had been increased from 98.61%, as reported in Example 4, to 99.79%, as reported in Example 7, at a feed temperature of 236° C.

Comparison of Examples 1, 5 and 6 shows that in the interval between Examples 1 and 5 the catalyst had dropped in activity from an arbitrary relative activity value of 100% in Example 1, as measured by conversion of dimethyl 1,4-cyclohexanedicarboxylate, to a relative catalyst activity of 87.63%, measured on the same basis in Example 5. After the reactivation procedure the relative catalyst activity, as reported in Example 6, had been restored to 94.19% of the original value.

TABLE II

| Example No. | Inlet Temp. °C. | Gas:DMCD Molar ratio | LHSV h$^{-1}$ | Pressure psia (bar) | DMCD conversion mol % | Selectivity mol % | | | |
|---|---|---|---|---|---|---|---|---|---|
| | | | | | | CHDM | BYPR | METH | DETH |
| 1 | 220 | 691 | 0.42 | 900 (62.05) | 97.53 | 96.89 | 2.75 | 0.14 | 0.14 |
| 2 | 230 | 381 | 0.31 | 903 (62.26) | 98.99 | 96.50 | 3.20 | 0.19 | 0.11 |
| 3 | 233 | 340 | 0.31 | 903 (62.26) | 99.06 | 96.54 | 3.16 | 0.19 | 0.11 |
| 4 | 236 | 354 | 0.30 | 906 (62.47) | 98.61 | 96.46 | 3.24 | 0.21 | 0.09 |
| 5 | 220 | 716 | 0.42 | 900 (62.05) | 85.47 | 96.63 | 3.15 | 0.11 | 0.11 |
| 6 | 219 | 715 | 0.41 | 900 (62.05) | 91.86 | 96.78 | 2.85 | 0.11 | 0.17 |
| 7 | 236 | 330 | 0.29 | 901 (62.12) | 99.79 | 95.74 | 3.84 | 0.24 | 0.18 |

Notes to Table II:
DMCD = dimethyl 1,4-cyclohexanedicarboxylate
LHSV = liquid hourly space velocity
CHDM = 1,4-cyclohexanedimethanol
BYPR = miscellaneous byproducts
METH = 4-methoxymethyl cyclohexanemethanol
DETH = di-(4-hydroxymethylcyclohexylmethyl) ether
Gas = hydrogen-containing gas containing more than 98% v/v hydrogen

Examples 8 to 12

The general procedure of Examples 1 to 7 is repeated using dimethyl maleate, diethyl maleate, diethyl succinate, dimethyl fumarate, or gamma-butyrolactone in place of dimethyl 1,4-cyclohexane-dicarboxylate, resulting in each case in production of butane-1,4-diol. A similar improvement in catalyst activity is observed following the reactivation procedure.

Example 13

The general procedure of Examples 1 to 7 is repeated except that catalyst A is replaced by catalyst B with similarly good results.

We claim:

1. A process for the production of alcohols and diols by hydrogenation of a corresponding unsaturated organic compound selected from esters, diesters and lactones which comprises:
   (a) providing a hydrogenation zone containing a charge of a granular copper-containing ester hydrogenation catalyst;
   (b) supplying to the hydrogenation zone, in a first phase of operation, a vaporous feed stream comprising a hydrogen-containing gas and an unsaturated organic compound selected from $C_1$ to $C_4$ alkyl esters of $C_8$ to $C_{22}$ alkylcarboxylic acids, di-($C_1$ to $C_4$) diesters of $C_4$ to $C_{16}$ dicarboxylic acids, gamma-butyrolactone and epsilon-caprolactone;
   (c) maintaining the hydrogenation zone, in the first phase of operation, at a temperature in the range of from about 150° C. to about 350° C. and a pressure in the range of from about 150 psia up to about 2000 psia;

(d) recovering from the hydrogenation zone, in the first phase of operation, a reaction product stream comprising the alcohol or diol;

(e) supplying to the hydrogenation zone, in a second phase of operation, a stream of hydrogen-containing gas which is substantially free from the unsaturated organic compound at an effective reactivation temperature and for an effective period of time thereby to reactivate the charge of copper-containing ester hydrogenation catalyst therein.

2. A process according to claim 1, in which the stream of hydrogen-containing gas of step (e) comprises a hot stream of recycle and make-up gas.

3. A process according to claim 1, in which the vaporous hydrogen-containing stream of the unsaturated organic compound of step (b) is substantially saturated with the unsaturated organic compound.

4. A process according to claim 3, in which the vaporous feed stream of step (b) is at a feed temperature at least about 5° C. above its dew point.

5. A process according to claim 1, in which the temperature and pressure of step (c) comprise a temperature of from about 150° C. to about 300° C. and a pressure of from about 450 psia (about 31.03 bar) to about 1000 psia (about 68.95 bar) and the copper containing hydrogenation catalyst is reduced copper chromite catalyst wherein the Cu:Cr weight ratio is from about 0.1:1 to about 4:1; reduced, copper chromite catalyst wherein the Cu:Cr weight ratio is from about 0.1:1 to about 4:1 promoted with from about 0.1% by weight up to 15% by weight of barium, manganese or a mixture of barium and manganese; or reduced manganese promoted copper catalyst wherein the Cu:Mn weight ratio is from about 2:1 to about 10:1.

6. A process according to claim 5, in which the unsaturated organic compound comprises dimethyl 1,4-cyclohexanedicarboxylate and in which the hydrogenated product comprises 1,4-cyclohexanedimethanol.

7. A process according to claim 5, in which the unsaturated organic compound comprises dimethyl 1,2-cyclohexanedicarboxylate and in which the hydrogenated product comprises 1,2-cyclohexanedimethanol.

8. A process according to claim 5, in which the unsaturated organic compound comprises dimethyl 1,3-cyclohexanedicarboxylate and in which the hydrogenated product comprises 1,3-cyclohexanedimethanol.

9. A process according to claim 5, in which the unsaturated organic compound comprises an ester selected from dimethyl and diethyl maleate and in which the hydrogenated product comprises butane-1,4-diol.

10. A process according to claim 5, in which the unsaturated organic compound comprises gamma-butyrolactone and the hydroxy compound comprises butane-1,4-diol.

11. A process according to claim 5, in which the period used for reactivation ranges from about 1 hour up to about 24 hour.

12. A process according to claim 5, in which the reactivation temperature of step (e) lies in the range of from about 150° C. to about 350° C. and is from about 50° C. less than to about 50° C. more than the feed temperature of the vaporous feed stream to the hydrogenation zone.

13. A process according to claim 5, in which the copper-containing catalyst is selected from reduced copper chromite, reduced promoted copper chromite, and manganese promoted copper catalysts.

14. A process for reactivating an at least partially deactivated copper-containing ester hydrogenation catalyst which has undergone deactivation through use in hydrogenation of an unsaturated organic compound selected from esters of $C_8$ to $C_{22}$ monocarboxylic acids, diesters of dicarboxylic acids, and lactones, to yield a corresponding hydroxylic compound selected from alcohols and diols which comprises contacting the at least partially deactivated copper-containing catalyst at an effective reactivation temperature and for an effective period of time with a stream of hydrogen-containing gas which is substantially free from the unsaturated organic compound thereby to reactivate the at least partially deactivated copper-containing catalyst.

15. A process for reactivating an at least partially deactivated copper-containing ester hydrogenation catalyst which has undergone deactivation through use in hydrogenation of an unsaturated organic compound selected from $C_1$ to $C_4$ alkyl esters of $C_8$ to $C_{22}$ monocarboxylic acids, di-($C_1$ to $C_4$) diesters of $C_4$ to $C_{16}$ dicarboxylic acids, gamma-butyrolactone and epsilon-caprolactone, to yield a corresponding alcohol or diol which comprises contacting the at least partially deactivated copper-containing catalyst at an effective reactivation temperature and for an effective period of time with a stream of hydrogen-containing gas which is substantially free from the unsaturated organic compound thereby to reactivate the at least partially deactivated copper-containing catalyst.

16. A process according to claim 15 for reactivating an at least partially deactivated copper-containing ester hydrogenation catalyst wherein the copper containing hydrogenation catalyst is reduced copper chromite catalyst wherein the Cu:Cr weight ratio is from about 0.1:1 to about 4:1; reduced, copper chromite catalyst wherein the Cu:Cr weight ratio is from about 0.1:1 to about 4:1 promoted with from about 0.1% by weight up to 15% by weight of barium, manganese or a mixture of barium and manganese; or reduced manganese promoted copper catalyst wherein the Cu:Mn weight ratio is from about 2:1 to about 10:1.

* * * * *